United States Patent [19]

Schumann

[11] Patent Number: Plant 5,929

[45] Date of Patent: Apr. 7, 1987

[54] GERANIUM PLANT NAMED MERCURY

[75] Inventor: Ingeborg Schumann, Bad Ems, Fed. Rep. of Germany

[73] Assignee: Fischer Geraniums, Inc., Netherlands Antilles

[21] Appl. No.: 761,009

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Mercury having red flower color; semi-double flower form; fast rooting; compact growth habit with excellent branching; good chlorophyll quality for transportation; relatively small leaves, and good temperature tolerance.

1 Drawing Figure

The present invention comprises a new and distinct cultivar of geranium, botanically known as *Pelargonium zonale*, and hereinafter referred to by the cultivar named Mercury.

Mercury is a product of a planned breeding program which had the objective of creating new geranium cultivars having red flower color, semi-double flower form, fast rooting, good temperature tolerance, and vigorous growth habit.

Mercury was originated from a hybridization made by Ingeborg Schumann in a controlled breeding program in Hillscheid, Federal Republic of Germany in 1979. The female parent was an inbred line of Alex. The male parent of Mercury was Bundeskanzler, which has red single flowers and inferior temperature tolerance and rooting habit. Both parents are unpatented.

Mercury was discovered and selected as one flowering plant within the progeny of the stated cross by Ingeborg Schumann in June of 1980 in a controlled environment in Hillscheid, Federal Republic of Germany.

The first act of asexual reproduction of Mercury was accomplished when vegetative cuttings were taken from the initial selection in January of 1981 in a controlled environment in Hillscheid, Federal Republic of Germany by a technician working under formulations established and supervised by Ingeborg Schumann. Horticultural examination of selected units initiated in the spring of 1981 and continuing in 1982 and 1983 has demonstrated that the combination of characteristics as herein disclosed for Mercury are firmly fixed and are retained through successive generations of asexual reproduction.

Mercury has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Mercury, which in combination distinguish this geranium as a new and distinct cultivar.

1. Red flower color.
2. Semi-double flower form.
3. Compact growth habit, with excellent branching.

4. Good chlorophyll quality for transportation.
5. Fast rooting.
6. Good temperature tolerance.
7. Relatively small leaves.

Of the many commercial cultivars known to the present inventor, the most similar in comparison to Mercury is Vesuv. Reference is made to the attached Chart A which compares certain characteristics of Mercury to those same characteristics of Vesuv. In comparison to Vesuv, Mercury has a brighter red color, better chlorophyll quality for transportion, longer peduncle length, and more vigorous growth.

The accompanying photographic drawing shows typical flower and foliage characteristics of Mercury, with colors being as true as possible with illustrations of this type.

In the following description colour references are made to The Royal Horticultural Society Color Chart. The color values were determined between 11:00 a.m. and 12:00 noon on May 22, 1985 under 40,000 Lux light intensity at Hillscheid, Federal Republic of Germany.

Classification:

*Botanical.*—A hybrid of the genus *Pelargonium l'hert* and species *Pelargonium zonale.*

*Commercial.*—Mercury.

INFLORESCENCE

A. Umbel:

*Average diameter.*—117 mm.

*Average depth.*—69 mm.

*Peduncle length.*—205 mm.

*Pedicel length.*—28 mm.

B. Corolla:

*Average diameter.*—50 mm.

*Form.*—Semi-double; asymmetric.

*Color (general tonality from a distance of three meters).*—Red. Upper surface: 44A.

C. Bud:

*Shape.*—Oval; somewhat pointed top.

*Color.*—Light purple to red.

D. Reproductive organs:

*Androecium.*—4–8 stamens.

*Gynoecium.*—5–6 lobed stigma.

E. Spring flowering response period: In Hillscheid, Federal Republic of Germany, in 1982, 45% of plants opened with at least one flower 13 weeks after planting of unrooted cuttings.

F. Outdoor flower production: The total flower count in 1982 in Hillscheid, Federal Republic of Germany, was between 47 and 50 flowers per plant for the June through October observation period.

G. Durability: Good.

PLANT

A. Foliage:

*Form.*—Kidney shaped.

*Margin.*—Wavy, slightly serrated.

*Color.*—Top surface: Medium to dark green, approximately 137A–C. Zonation: none.

*Tolerance of botrytis.*—Good.

B. General appearance and form:

*Internode length.*—26 mm.

*Branching pattern.*—3.1 branches per plant.

*Height.*—220 mm.

CHART A

| CULTIVAR | COROLLA COLOR | PEDUNCLE LENGTH |
|---|---|---|
| Mercury | RHS 44A | 205 mm |
| Vesuv | RHS 43B | 200 mm |
| **CULTIVAR** | **UMBEL AVERAGE** | **LEAF COLOR** |
| Mercury | 117 mm | Medium to dark green |
| Vesuv | 109 mm | Medium to light green |

I claim:

1. A new and distinct cultivar of geranium named Mercury, as described and illustrated, and particularly characterized by its red flower color; semi-double flower form; fast rooting; compact growth habit with excellent branching; good chlorophyll quality for transportation; relatively small leaves, and good temperature tolerance.

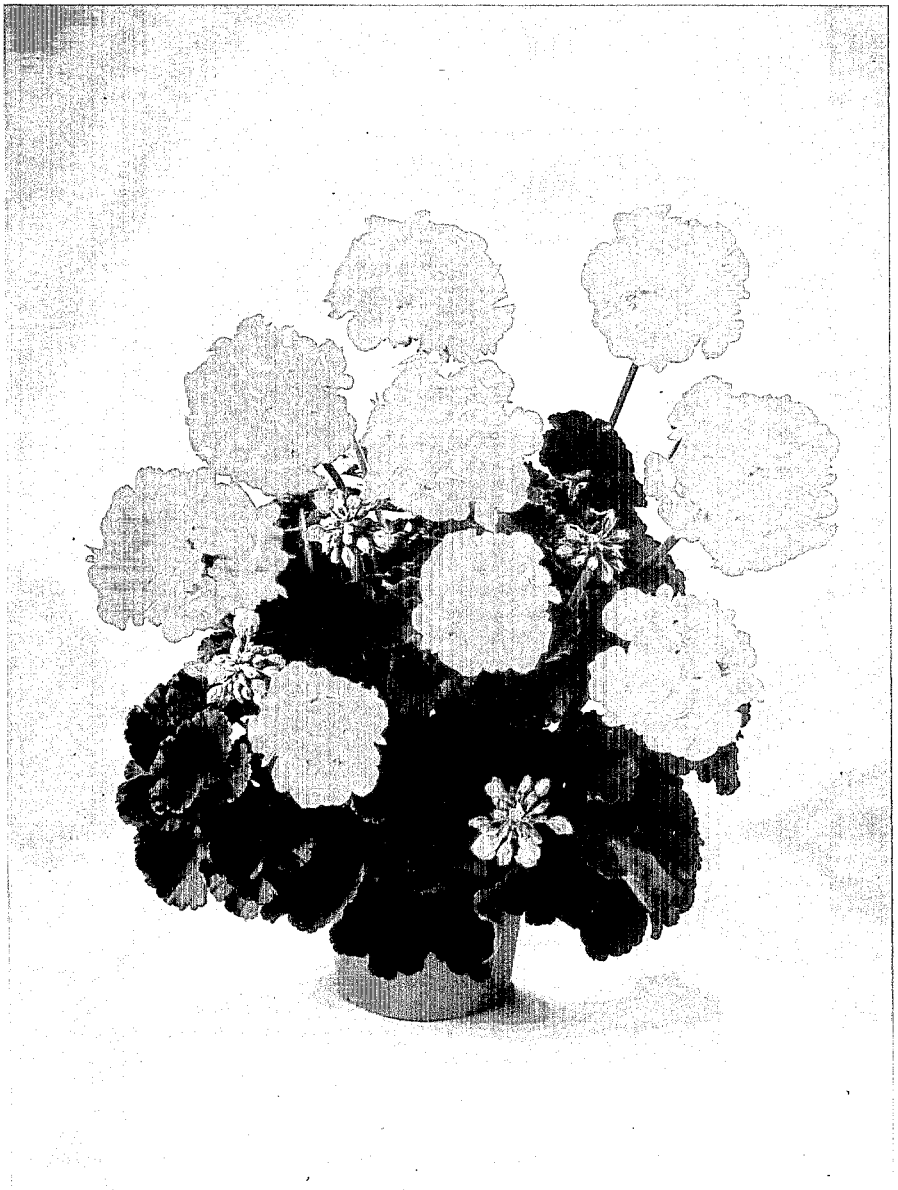

* * * * *